United States Patent
Nakatsu et al.

(10) Patent No.: US 6,780,443 B1
(45) Date of Patent: Aug. 24, 2004

(54) SENSATE COMPOSITION IMPARTING INITIAL SENSATION UPON CONTACT

(75) Inventors: Tetsuo Nakatsu, Chappaqua, NY (US); Peter J. Mazeiko, Middletown, NY (US); Andrew T. Lupo, Jr., Emerson, NJ (US); Carter B. Green, Stony Point, NY (US); Charles H. Manley, Ringwood, NJ (US); David J. Spence, Ridgefield Park, NJ (US); Hideaki Ohta, Kanagawa (JP)

(73) Assignees: Takasago International Corporation, Tokyo (JP); Takasago International Corporation (USA), Rockleigh, NJ (US)

( * ) Notice: Subject to any disclaimer, the term of this patent is extended or adjusted under 35 U.S.C. 154(b) by 0 days.

(21) Appl. No.: 09/498,592

(22) Filed: Feb. 4, 2000

(51) Int. Cl.[7] .................. A61K 7/16; A61K 31/075; A23L 1/22
(52) U.S. Cl. .................. 424/734; 424/725; 424/747; 426/540; 426/536; 514/718
(58) Field of Search ................. 514/783, 729, 514/718, 719; 424/76.9; 426/651, 650

(56) References Cited

U.S. PATENT DOCUMENTS

| | | | |
|---|---|---|---|
| 3,720,762 A | 3/1973 | Hatasa | 424/58 |
| 4,029,759 A | 6/1977 | Humbert et al. | 424/49 |
| 4,374,824 A | 2/1983 | Wahmi | 424/58 |
| 4,459,425 A | 7/1984 | Amano et al. | 426/536 |
| 4,980,169 A | * 12/1990 | Oppenheimer et al. | 424/439 |
| 5,035,882 A | * 7/1991 | Hussein et al. | 424/58 |
| 5,545,424 A | 8/1996 | Nakatsu et al. | 426/536 |

FOREIGN PATENT DOCUMENTS

| | | | |
|---|---|---|---|
| CA | 1133831 | 10/1982 | ............ A61K/7/16 |
| EP | 1438205 | 8/1974 | ............ A61K/7/16 |
| EP | 0452273 | 4/1991 | .......... A61K/35/78 |
| GB | 1315626 | 5/1973 | |
| GB | 2098476 | 5/1981 | ............ A61K/7/16 |
| JP | 54067040 A | 5/1979 | |
| JP | 86009293 B | 3/1986 | |
| WO | WO97/02273 | * 1/1997 | |
| WO | WO 97/06695 | 2/1997 | ............ A23G/3/00 |
| WO | WO 98/47482 | 10/1998 | ............ A61K/9/00 |

OTHER PUBLICATIONS

Journal of the Society of Cosmetics Chemists, 29, 185–200, 1978; "New Compounds With Menthol Cooling Effect", H.R, Watson et al.

Journal of Pharmacy and Pharmacology, 46, 618–630, 1994, "Menthol and Related Cooling Compounds", R. Eccles.

Environment, Drugs, and Thermoregulation, 5th Int. Symp. Pharmacol. Thermoregulation, Saint–Paul–de Vence, 183–186, 1982, "AG–3–5: A Chemical Which Produces Sensations of Cold", E.T. Wei.

Tetrahedron Letters, vol. 28, No. 18, pp 2215–2218, 1988, Great Britain, "A Direct Synthesis of Cyclic Acetals From β– OR γ–Hydroxy Ethers By Means of C–H Activation", K. Furata et al.

* cited by examiner

Primary Examiner—Vickie Kim
(74) Attorney, Agent, or Firm—Darby & Darby

(57) ABSTRACT

The present invention is directed to a sensate composition including at least one cooling sensate, warming sensate and tingling sensate. The tingling sensate is at least one of Jambu Oleoresin and Spilanthol. The present invention is further directed to a method of using the sensate composition in a food, pharmaceutical or personal care product.

1 Claim, No Drawings

SENSATE COMPOSITION IMPARTING INITIAL SENSATION UPON CONTACT

BACKGROUND OF THE INVENTION

The present invention relates to a composition imparting an initial sensation similar to tingling upon first contact. More specifically, the present invention is a composition including a cooling sensate, a warming sensate and a tingling-type sensate, which when used in combination, imparts an immediate initial sensation. The initial sensation can best be described as a tingling or a stinging impression which also enhances the sensation of the other sensates used in the composition. In addition, the composition of the present invention also helps moderate the harsh and stimulative effects of the cooling agents. This moderation of the harsh effects of cooling agents is referred to herein as an emollient effect.

Various types of products incorporate ingredients which impart some kind of sensation to the mucous membranes, oral cavity, throat or skin. These ingredients may be used as flavors or fragrances in a wide range of products such as personal care products (perfumes deodorants, cosmetics, shampoos, skin creams, toothpastes and the like), pharmaceuticals (such as cough syrups, cough drops and the like) and foods (such as chewing gum, soda and the like).

For example, 1-menthol and 3-(1-menthoxy)propane-1,2-diol are used as active ingredients in products to impart a cooling sensation to the mouth or skin (U.S. Pat. No. 4,459,425). However, 1-menthol has the drawback of being very volatile as well as irritating to skin and mucous membranes. There is a limit to how much 1-menthol can be used in a product to produce a cooling sensation, because when used in greater amounts the 1-menthol becomes very harsh and irritating. Much research has been done to find alternatives to menthol as a cooling agent. In *New Compounds with the Menthol Cooling Effect*, J. Soc. Cosmet. Chem., 29: 185–200 (1978), by H. R. Watson et al., the physiological basis for the cooling effect of menthol is discussed. In addition, certain important molecular requirements were described that are believed to be necessary in order for a compound to have the desired effect. Several N-alkyl-carboxamide compounds were found to possess the cooling sensation of menthol while having the advantage of being less volatile. The pharmacology and toxicology of menthol use in various products and for various modes of administration has also been reported. See *Menthol and Related Cooling Compounds*, J. Pharm. Pharmacol., 46: 618–630 (1994), by R. Eccles. Another alternative to menthol is 1(2-hydroxyphenyl)-4-(3-nitrophyenyl)-1,2,3,5-tetrahydropyrimidine-2-one. This compound is discussed in *A Chemical Which Produces Sensations of Cold*, Environment, Drugs and Thermoregulation, 5th International Symp. Pharmacol. Thermoregulation, Saint-Paul-de-Vence, 1982, pp. 183–186 (Karger, Basel, 1983) by E. T. Wei.

Other known physiological cooling agents including peppermint oil, N-substituted-p-menthane-3-carboxamides, acyclic tertiary and secondary carboxamides, 3-1-menthoxy propan-1,2-diol have also been reported (See PCT Published Application Number WO 97/06695).

Heating and/or warming sensates are also known. Vanillyl alcohol n-butyl ether (vanillyl butyl ether) is known as an active ingredient in products to impart a sharp, tangy bite or a heating/warming sensation (Japanese Laid-Open Application No. 54-67040). A formulation for cough drops has been reported which includes a physiological cooling agent and a physiological warming agent (PCT Published Application No. 1WO 97/06695). Physiological cooling agents disclosed therein include peppermint oil, N-substituted-p-menthane-3-carboxamides, acyclic tertiary and secondary carboxamides, 3–13menthoxy propan-1,2-diol. Physiological warming agents disclosed therein include vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, chloroform, eugenol, cinnamon oil, connamic aldehyde and phosphate derivatives of same.

A compound that possesses a hot, burning and tingling taste that is long lasting has been reported as 4-(1-methoxymethyl)-2-phenyl- 1,3-dioxolane or its derivatives represented by the following general formula (I):

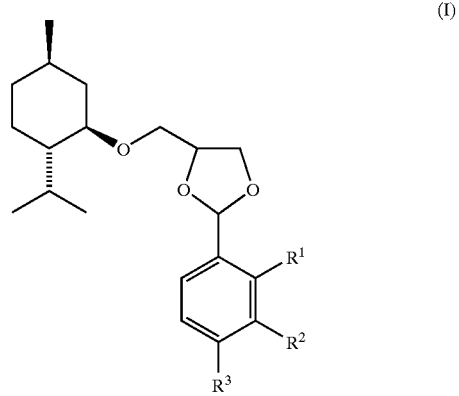

wherein $R^1$ represents a hydrogen atom, a hydroxy group or a lower alkoxy group, $R^2$ and $R^3$, which may be the same or different, each represent a hydrogen atom, a hydroxy group, a lower alkoxy group, or when taken together, R2 and R3 represent a methylene dioxy group. See U.S. Pat. No. 5,545,424 which is herein incorporated by reference. This warming sensate was also reported to prolong the sensations of certain cooling sensates, for example in combination with 1-menthol, 3-(-1-menthoxy)-1,2-propanediol ("TK-10" by Takasago International Corp., Tokyo, Japan) or isopulegol. The combination of the cooling and warming sensates signaled prolonged cooling effects to the user. Thus, the burning, tingling or bitter sensations associated with this warming sensate were able to convey to the user a better appreciation of the cooling sensate.

In addition, vanillyl alcohol n-butyl ether (vanillyl butyl ether) is known as an active ingredient in products to impart a sharp, tangy bite or a heating/warming sensation (Japanese Laid-Open Application No. 54-67040 and Examined Japanese Patent Application No. 61-9293).

Certain materials are known to cause a tingling, numbing and/or stinging sensation and are used in foods as popular spice and/or herb condiments. These include Jambu Oleoresin or para cress (Spilanthes sp.) the active ingredient being Spiranthol; Japanese pepper extract (*Zanthoxylum peperitum*) having the active ingredient(s) known as Saanshool-I, Saanshool-II and Sanshoamide, Black pepper extract (*Piper nigrum*) having the active ingredients Chavicine and Piperine.

It is also known to combine compounds known to possess flavor and/or sensate compounds to produce new active ingredients having altered properties. For example, PCT published application WO 98/47482 discloses formulations for cough drops which include a physiological cooling agent (such as menthol, peppermint oil, n-N-substituted-p-menthane-3-carboxamides, acyclic tertiary and secondary carboxamides, 3-1-menthoxy propan-1,2-diol) and a physiological warming agent (such as vanillyl alcohol n-butyl ether, vanillyl alcohol n-propyl ether, vanillyl alcohol isopropyl ether, vanillyl alcohol isobutyl ether, vanillyl alcolol n-amino ether, vanillyl alcohol isoamyl ether, vanillyl alcohol n-hexyl ether vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, chloroform, eugenol, cinnamon oil, cinnamic aldehyde and phosphate derivatives of same.

Use of vanillyl butyl ether in combination with a cooling agent is disclosed in co-pending application entitled "COOL FEELING COMPOSITION" filed on or about Aug. 4, 1999 by one or more of the inventors of the present invention. The composition disclosed therein imparts a refreshing sensation in various consumer products.

The known cooling, warming and combination sensate compounds tend to have a lag time between first contact and when the sensate is first detected. It is often seconds before the sensation is actually perceived by the user. In addition, the cooling and warming sensate compounds, and combinations thereof that are known to date, do not last very long. It is often only a few seconds or minutes before the sensation wanes. It is desirable to have a cooling, warming or combination sensate compound that is perceived by the user immediately upon first contact with the user. It is also desirable for the perceived sensation to last for a greater duration of time than just the first few seconds or so.

OBJECTS AND SUMMARY OF THE INVENTION

It is an object of the present invention to provide a taste and touch sensate that overcomes the limitations of the prior art.

It is an object of the present invention to provide a sensate compound that provide a strong initial signal to the user.

It is a further object of the present invention to provide a sensate compound that provides a tingling and/or stinging impression upon contact.

It is a further object of the present invention to provide a sensate compound that provides lasting sensation beyond first contact.

It is a further object of the present invention to provide a sensate compound that provides an emollient effect on one or more stimulative co-ingredients.

After extensive research, the inventors of the present invention have discovered that combining cooling sensates with warming sensates and a tingling sensate (such as Jambu oleoresin or Spilanthol), results in enhancement of the flavor and/or sensation of the cooling and/or warming sensates. In addition, this combination has been shown to initiate perception of the flavor of the sensates in a shorter period of time than occurs when either the cooling sensate, the warming sensate, or a combination of the two are used without the tingling sensate.

Briefly stated, the present invention is a sensate composition including at least one cooling sensate, at least one warming sensate and at least one tingling sensate.

In an embodiment of the present invention, a method of using a sensate compositon as at least one of a fragrance and a flavor is provided, which includes forming a sensate composition having at least one cooling sensate, at least one warming sensate and at least one tingling sensate containing effective amounts of the sensates and admixing the sensate composition with a suitable carrier.

The above, and other objects, features and advantages of the present invention will become apparent from the following description. However, these examples are not to be construed to limit the scope of the invention.

DETAILED DESCRIPTION OF THE PREFERRED EMBODIMENT

As described above, 1-menthol, 3-(1-menthoxy)propane-1,2-diol and other compounds are known cooling agents. In addition, vanillyl butyl ether is known as a warming sensate. Jambu oleoresin is an extract used to impart tingling flavor in foods.

In the new sensate of the present invention, vanillyl butyl ether is combined with a cooling sensate and a warming sensate to impart an immediate sensation upon contact that also provides an emollient effect on the cooling sensate. The cooling sensate can be a single cooling sensate or a combination of different cooling sensates. The warming sensate can be a single such sensate or a combination thereof.

There are no specific limitations to the relative amounts of the compounds of the composition. However, it is preferred that vanillyl butyl ether is used in a relative amount with respect to the cooling agent so that no discernable warming effect occurs. Preferably, vanillyl butyl ether is used on a weight basis, from 1/1000 to 2 times as much as the cooling agent. More preferably, the vanillyl butyl ether is present in the composition from 1/200 to 1 times the amount of the cooling agent on a weight basis.

The new sensate composition of the present invention may further contain diluents (ethanol, purified water, etc.) which are safe for use in products used for consumption and/or topical use. The new sensate composition of the present invention can be used in various products to which the qualities of the sensate are desirable. Examples of suitable products include: cosmetics (such as lipstick, after shave lotions, foundation and the like), personal care products (such as skin creams, astringent lotions, cleansing lotions, deodorants, shampoos, conditioners, soaps, hair gels, hair tonics, hair growth stimulants, shaving foams, shaving creams, bubbling bath beads and the like) and pharmaceutical compositions (such as insect repellent sprays, hair tonics, analgesic preparations, lozenges and the like). These are set forth as examples, however the products in which the composition of the present invention may be used are not limited to these.

The amount of the sensate composition of the present invention in a product varies widely depending on the amount of the product used at one time and the manner in which it is used or applied. In general, the content of the sensate composition any be from 0.001 to 20% by weight, preferably from 0.01 to 10% by weight of the entire product composition. However, the sensate composition may be added to a product in any amount, as long as the effect of the composition is present. The sensate composition may be made first, then added to a product. Alternatively, the cooling agent, warming agent and tingling agent may be added separately to the product.

The present invention will be described in greater detail by reference to the following Embodiments and Comparative Examples, however, it should be noted the invention is not limited to these examples.

Embodiment 1

Embodiment 1 was prepared by mixing N-ethyl-2-isopropyl-5-methylcyclohexane carboxamide as a cooling agent, vanillyl butyl ether as a warming agent and Jambu Oleoresin as a tingling agent with other ingredients according to the following formulation to produce a mouthwash. These ingredients are prepared according to methods that are known in the art.

| Ingredient | Percentage (%) in flavors |
| --- | --- |
| ethyl alcohol | 55.0 |
| propylene glycol | 28.0 |
| N-ethyl-2-isopropyl-5-methylcyclohexane carboxamide | 3.0 |
| isopulegole | 8.0 |
| Jambu Oleoresin | 2.5 |
| vanillyl butyl ether | 3.0 |
| mouthwash herbal flavor base | 0.5 |

A sensory evaluation was performed on the mouthwash of Embodiment 1. Eight members of a panel trained as Flavorists evaluated the products. They found that the blend produced a unique flavor and taste profile. Members of the panel reported a tingling sensation upon first contact with the mouthwash. No delay in perceived sensation was reported.

COMPARATIVE EXAMPLE 1

Comparative Example 1 was made in the same manner as Embodiment 1, except that Jambu Oleoresin was omitted.

A taste panel was convened to evaluate any perceived differences in character between the mouthwash of Embodiment 1 and Comparative Example 1. Panelists were asked to compare the flavor sensation of the two products and comment on any differences.

The majority of the panelists noted that there was a distinct difference in warming sensation perception and onset. The coded sample containing the Jambu Oleoresin was described as having a fuller warming, tingling effect as compared to the Jambu free system which was less complex and less stimulating with an almost retarded onset of the cooling perception. There was a noted synergistic effect between the ingredients. The profiles were described as a significant tingling and an enhancement of the cooling and warming perception of the product. The study showed that all three components, cooling, heating and tingling are necessary to produce the observed unique effect.

Embodiment 2

Embodiment 2 was prepared by mixing 3-(-1-menthoxy)-1,2 propanediol ("TK-10" from Takasago, Takasago International Corp., Tokyo, Japan) as a cooling agent, capiscum oleoresin as a warming agent and Jambu Oleoresin as a tingling agent with other ingredients according to the following formulation to make a toothpaste according to methods that are known in the art.

| Ingredient | Percentage |
| --- | --- |
| ethanol | 48.0 |
| Benzyl alcohol | 34.0 |
| Jambu Oleoresin | 10.0 |
| Ginger Oleoresin | 2.0 |
| Capsicum Oleoresin | 0.5 |
| 3-(-1-menthoxy)-1,2-propanediol ("TK-10") | 2.0 |

COMPARATIVE EXAMPLE 2

Comparative Example 2 was prepared in the same manner as Embodiment 2, except Jambu Oleoresin was omitted.

A select taste panel evaluated the perceived differences in character between the toothpaste preparation of Embodiment 2 and Comparative Example 2. Panelists were asked to compare the flavor sensation of the two products and comment on any differences. Evaluations were performed blind.

The majority of the panelists noted that the sample containing the tingling sensate material had quicker tingling sensation onset and an enhanced, prolonged cool, tingling, pleasant aftertaste. Panelists for the most part perceived Comparative Example 2 to be pleasant but lacking in the robustness and impact of Embodiment 2.

Embodiment 3

Embodiment 3 was prepared by mixing 4-(1-menthoxymethyl)-2,3'-methoxy-4'-hydroxyphenyl)-1,3-dioxolane, ginger oleoresin, vanillyl butyl ether and Jambu Oleoresin with other ingredients according to the following candy formulation which was prepared in accord with methods well known in the art.

| Ingredient | Percentage |
| --- | --- |
| medium chain triglycerides | 82.0 |
| vanillyl butyl ether | 7.5 |
| ginger oleoresin | 3.1 |
| capsicum oleoresin | 0.1 |

-continued

| Ingredient | Percentage |
|---|---|
| 4-(1-menthoxy-methyl)-2,3'-methoxy-4'-hydroxyphenyl)-1,3-dioxolane | 4.0 |
| menthol | 1.0 |
| Jambu Oleoresin | 3.0 |

COMPARATIVE EXAMPLE 3

Comparative Example 3 was prepared in the same manner as Embodiment 3, except no Jambu Oleoresin was used.

A panel group was convened to evaluate Embodiment 3 and Comparative Example 3 in random blind fashion and comment on any noted differences. Eight members of a panel trained as Flavorists evaluated the product. Members of the panel reported a tingling sensation upon first contact with the candy. No delay in perceived sensation was reported. Analysis of panelists comments showed a marked enhancement of the warming sensation was realized in Embodiment 3 as compared to Comparative Example 3. The onset of the flavor was more pronounced in Embodiment 3 than in Comparative Example 3. Panelists observed Comparative Example 3 seemed to be less bright and slower to exhibit any unique sensations.

Embodiment 4 (E4)

Embodiment 4 was prepared by mixing menthol, 3-(1,2-menthoxy) propane-1,2-diol, vanillyl butyl ether and Jambu Oleoresin with other ingredients according to the following formulation. A cosmetic cologne or other similar product may be prepared from this formulation by admixture with known ingredients in accord with formulations well known in the art.

COMPARATIVE EXAMPLE 4 (CE4)

Comparative Example 4 was made in the same fashion as Embodiment 4, except that Jambu Oleoresin was omitted.

COMPARATIVE EXAMPLE 5 (CE5)

Comparative Example 5 was made in the same fashion as Embodiment 4, except that vanillyl butyl ether was omitted.

| | Amount (% by weight) | | |
|---|---|---|---|
| Ingredient | E 1 | CE 1 | CE 2 |
| menthol | 0.50 | 0.50 | 0.50 |
| 3-(1,2-menthoxy) propane-1,2-diol | 0.50 | 0.50 | 0.50 |
| Vanillyl butyl ether | 0.05 | 0.05 | — |
| Jambu extract (10% solution) | 0.50 | — | 0.50 |
| Ethanol (50% solution) | 98.45 | 98.50 | 98.45 |

A formal panel evaluated Embodiment 4 and Comparative Examples 4 and 5 according to the following protocol. 0.1 ml of the composition was placed on a patch cloth and applied to the forearm of each of the panelists. The sensate compositions were evaluated for their relative performance in the following categories: cooling sensate, stimulation, emollient and comfort/preference. The results are reported in Table 1.

TABLE 1

| Panelist (A–C) and Time Course | Cooling Sensate | Stimulation | Emollient | Comfort/ Preference |
|---|---|---|---|---|
| 0 minutes | | | | |
| A | CE4 > E5 > CE5 | CE4 > E5 > CE5 | CE5 > E5 > CE4 | E5 > CE5 = CE4 |
| B | E5 = CE4 > CE5 | CE4 > E5 > CE5 | CE5 = E5 > CE4 | E5 > CE5 > CE4 |
| C | E5 = CE4 > CE5 | CE4 > E5 > CE5 | CE5 > E5 > CE4 | E5 > CE4 > CE5 |
| 5 minutes | | | | |
| A | CE4 > E5 > CE5 | CE4 > E5 > CE5 | CE5 > E5 > CE4 | E5 ≧ CE4 > CE5 |
| B | E5 = CE4 > CE5 | CE4 > E5 > CE5 | CE5 = E5 > CE4 | E5 > CE5 > CE4 |
| C | E5 = CE4 > CE5 | CE4 > E5 > CE5 | CE5 > E5 > CE4 | E5 > CE4 > CE5 |
| 10 minutes | | | | |
| A | CE4 > E5 > CE5 | CE4 > E5 > CE5 | CE5 > E5 > CE4 | E5 > CE5 = CE4 |
| B | CE4 > E5 > CE5 | CE4 > E5 > CE5 | CE5 = E5 > CE4 | E5 > CE4 > CE5 |
| C | E5 > CE4 = CE5 | CE4 > E5 > CE5 | CE5 = E5 > CE4 | E5 > CE4 = CE5 |

The results showed that the addition of Jambu Oleoresin increased the emollient effect on menthol and vanillyl butyl ether without losing cooling effect. Almost all panelists preferred Embodiment 4 over Comparative Examples 4 and 5.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A sensate composition which imparts an immediate sensation upon contact, consisting essentially of:
   a) from about 0.001% by weight to about 10% by weight of a cooling sensate substance selected from the group consisting of menthol, isopulegole, 3-(I-menthoxy) propan-1 2-diol, p-menthan-3,8-diol, 6-isopropyl-9-methyl-1,4-dioxaspiro-(4,5)-decane-2-methanol, menthyl succinate, alkaline earth salts of menthyl succinate, trimethyl cyclohexanol, N-ethyl-2-isopropyl-5-methylcyclohexane carboxamide, 3-(l-menthoxy)-2-methyl-propan-1,2-diol, mint oil, peppermint oil, wintergreen, menthone, menthone glycerin ketal, menthyl lactate, [1'R,2'S,5'R]-2-(5'-methyl-2'-(methylethyl) cyclohexyloxy)ethan-1-ol, [1'R,2'S,5'R]-3-(5'-methyl-2'-(methylethyl)cyclohexyloxy)propan-1-ol, [1'R,2'S,5'R]-4-(5'-methyl-2'-(methylethyl)cyclohexyloxy) butan-1-ol, spearmint, or mixture thereof;

b) from about 0.001% by weight to about 10% by weight of a warming sensate substance selected from the group consisting of vanillyl ethyl ether, vanillyl propyl ether, vanillin propylene glycol acetal, ethyl vanillin propylene glycol acetal, capsaicin, gingerol, vanillyl butyl ether, 4-(l-menthoxy-methyl)-2-phenyl-1,3-dioxolane, 4-(l-menthoxy-methyl)-2-(3',4'-dihydroxy-phenyl)-1,3-dioxolane, 4-(l-menthoxy-methyl)-2-(2'-hydroxy-3'-methoxy-phenyl)-1,3-dioxolane, 4-(l-menthoxy-methyl)-2-(4'-methoxyphenyl)-1,3-dioxolane, 4-(l-menthoxy-methyl)-2-(3'4'-methylenedioxy-phenyl)-1,3-dioxolane, hot pepper oil, capsicum oleoresin, ginger oleoresin, nonyl acid vanillylamide, 4-(l-menthoxy-methyl)-2-(3'-methoxy-4'-hydroxyphenyl)-1,3-dioxolane, or mixture thereof;

c) from about 0.001% by weight to about 10% by weight of a tingling sensate substance selected from the group consisting of Jambu Oleoresin, *Zanthoxylum peperitum* saanshool-I, saanshool II, sanshoamide, Spilanthol, or mixture thereof; and d) a diluent or carrier.

* * * * *

UNITED STATES PATENT AND TRADEMARK OFFICE
CERTIFICATE OF CORRECTION

PATENT NO.    : 6,780,443 B1
DATED         : August 24, 2004
INVENTOR(S)   : Tetsuo Nakatsu et al.

It is certified that error appears in the above-identified patent and that said Letters Patent is hereby corrected as shown below:

Title page,
Item [75], Inventor, please delete "Peter J. Mazeiko, Middletown, NY" and substitute -- Peter J. Mazeiko, Westchester, PA --.

Signed and Sealed this

Twenty-fifth Day of January, 2005

JON W. DUDAS
*Director of the United States Patent and Trademark Office*